United States Patent [19]
Biedermann et al.

[11] Patent Number: 5,980,921
[45] Date of Patent: *Nov. 9, 1999

[54] TOPICAL COMPOSITIONS FOR REGULATING THE OILY/SHINY APPEARANCE OF SKIN

[75] Inventors: Kimberly Ann Biedermann; George Endel Deckner, both of Cincinnati, Ohio

[73] Assignee: The Procter & Gamble Company, Cincinnati, Ohio

[ * ] Notice: This patent is subject to a terminal disclaimer.

[21] Appl. No.: 09/134,025

[22] Filed: Aug. 14, 1998

Related U.S. Application Data

[63] Continuation of application No. 08/554,067, Nov. 6, 1995, Pat. No. 5,833,998.

[51] Int. Cl.⁶ ..................................................... A61K 7/48
[52] U.S. Cl. ........................... 424/401; 424/69; 424/70.1; 514/844; 514/846; 514/944
[58] Field of Search ..................................... 424/401, 70.1, 424/69; 514/844, 846, 944

[56] References Cited

U.S. PATENT DOCUMENTS

| | | | |
|---|---|---|---|
| 5,688,831 | 11/1997 | El-Nokaly et al. | 514/938 |
| 5,833,998 | 11/1998 | Biedermann et al. | 424/401 |

*Primary Examiner*—Jyothsna Venkat
*Attorney, Agent, or Firm*—Darryl C. Little

[57] ABSTRACT

The present invention is directed to topical compositions for regulating the oil and/or shiny appearance of mammalian skin which comprise: a) from about 1% to about 10% of an active for regulating the oil and/or shiny appearance of mammalian skin which consists essentially of one or more compounds selected from the group consisting of niacinamide, panthenol, and pantothenic acid; and b) a cosmetically acceptable carrier for the active.

5 Claims, No Drawings

5,980,921

TOPICAL COMPOSITIONS FOR REGULATING THE OILY/SHINY APPEARANCE OF SKIN

CROSS REFERENCE

This application is a continuation of U.S. application Ser. No. 08/554,067, filed Nov. 6, 1995 now U.S. Pat. No. 5,833,998.

TECHNICAL FIELD

The present invention relates to topical compositions, and especially topical compositions for facial and scalp application. The topical compositions are particularly useful for regulating the oily and/or shiny appearance of skin.

BACKGROUND OF THE INVENTION

In the field of skin care compositions, the population is often classified by skin type, e.g., dry, normal, oily, combined dry/normal, combined dry/oily, or combined normal/oily skin (the latter two classes hereinafter alternatively referred to as "combined skin").

Persons with an oily skin type or combined skin type typically manifest an oily and/or shiny skin appearance between cleansings. This oily or shiny appearance generally increases as the day progresses following cleansing of the skin. In order to avoid such appearance, individuals must throughout the day either cleanse the skin, blot the skin, apply oil absorbing powders to the skin, or take some other measure to minimize the appearance of oil or shine.

Therefore, it has been desired in the art to provide topical compositions which minimize the appearance of oil and/or shine on the skin, especially oily or combined skin. Several topical compositions which are said to be designed for controlling oily and/or shiny skin are known in the art. For example, facial moisturizers and make-up said to have such property are known.

An oily or combined skin type presents a particular challenge to the formulation of make-up intended for facial use, including foundations. This is because as oil accumulates on the facial skin of such individuals, oil breakthrough occurs (the oil is not masked by the make-up such that an oily or shiny skin appearance results), and the coverage and wear resistance of the make-up tends to be reduced. It would be desirable to provide a make-up that maintains a high degree of coverage and wear resistance after application to all skin types, including oily and combined skin, preferably substantially as originally applied.

While certain formulations have been designed in an attempt to control the oily and/or shiny appearance of skin, there remains a need to provide improved topical compositions for minimizing the appearance of skin oil and/or shine. In addition to minimizing oil and/or shine, such compositions should not unacceptably discolor the skin. There is a particular need to provide improved facial make-up which minimizes the appearance of skin oil and/or shine, provides and maintains an even (i.e., uniform coverage) complexion and acceptable skin tone for extended periods after application, and/or which has extended wear resistance after application.

The B vitamins or vitamin B complex have heretofore been used to treat a number of conditions. For example, the following compounds have had the respective applications: riboflavin (acne, diabetes, anti-oxidant therapy, anemia, skin disorders, stress); nicotinic acid (atherosclerosis, pellegra, high cholesterol, high blood pressure, skin inflammation, antioxidant therapy); nicotinamide (pellegra, skin inflammation, anti-oxidant therapy); pantothenic acid (acne, anemia, arthritis, high cholesterol, atherosclerosis, alcohol detoxification, infections, hair loss); pyridoxine (acne, anemia, high cholesterol, skin inflammation, immune disorders, antioxidant therapy, carpal tunnel syndrome, premenstrual syndrome). These utilities and those of other B vitamin (complex) compounds are further described, along with a discussion of their contraindications and deficiency symptoms, in *The Doctor's Vitamin and Mineral Encyclopedia*, Hendler, S. S., pp. 49–82 (Simon & Schuster, New York 1990) and *Nutrients Catalog*, Newstrom, H., pp. 11–90 (McFarland & Co. 1993).

It has now been found that certain B vitamins are useful when topically applied for regulating the appearance of oily and/or shiny skin, including oily and combined skin, without unacceptably discoloring the skin, e.g., by unacceptable skin flushing or reddening. It has surprisingly been found that topical compositions containing these compounds in the form of a facial make-up composition minimize the appearance of skin oil and/or shine, provide and maintain substantially uniform coverage and an acceptable skin tone for extended periods after application, and/or have extended wear resistance after application.

It is an object of the present invention to provide topical compositions for regulating the oily and/or shiny appearance of mammalian skin, especially facial skin. It is a further object of this invention to provide such topical compositions which regulate the appearance of oily and/or shiny mammalian skin, provide and maintain substantially uniform coverage for extended periods after application to the skin, provide and maintain an acceptable skin tone for extended periods after application to the skin, and/or have extended wear resistance after application to the skin. Another object of the present invention is to provide methods of regulating the appearance of oily and/or shiny mammalian skin.

Other objects of the subject invention will be apparent from the disclosure which follows.

SUMMARY OF THE INVENTION

The present invention relates to topical compositions for regulating the oily and/or shiny appearance of mammalian skin, and especially facial skin. The compositions comprise a suitable active in an amount that is safe and effective for regulating the oily and/or shiny appearance of the skin, and a cosmetically acceptable topical carrier for the active. Preferred actives are those which effectively regulate the oily and/or shiny appearance of skin, and which do not unacceptably discolor the skin, e.g., unacceptably cause reddening or flushing of the skin. Suitable actives include those selected from the group consisting of niacinamide, pyridoxine, panthenol, pantothenic acid and mixtures thereof (these actives are alternatively referred to herein, individually or collectively, as "primary actives"). It has surprisingly been found that such actives, when topically applied to the skin, are especially useful for regulating the appearance of oily and/or shiny skin, including oily and combined skin, without unacceptably discoloring the skin, e.g., by unacceptable skin flushing or reddening. It has surprisingly been found that topical compositions containing these compounds in the form of a facial make-up composition minimize the appearance of skin oil and/or shine, provide and maintain substantially uniform coverage and acceptable skin tone for extended periods after application, and/or have extended wear resistance after application.

In preferred embodiments, the primary active comprises niacinamide. More preferably, the primary active consists essentially of niacinamide. Where niacinamide is used, it is preferably substantially pure niacinamide. The primary active is preferably used in an amount of from about 2.5% to about 5% by weight of the composition.

The present invention also relates to methods of regulating the oily and/or shiny appearance of mammalian skin by topical application of such compositions.

DETAILED DESCRIPTION OF PREFERRED EMBODIMENTS

The compositions of the present invention are useful as topical compositions, i.e., they are suitable for topical administration to a biological subject such as a mammal. As used herein, "topical" means applied to the surface of the skin. The compositions of the subject invention are administered topically to a biological subject, i.e., by the direct laying on or spreading of the composition on the skin of the subject.

The topical compositions comprise a safe and effective amount of one or more primary actives and a cosmetically acceptable topical carrier for the primary actives.

As used herein "comprising" means that other steps and ingredients which do not affect the end result can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

As used herein, "safe and effective amount" means a sufficient amount of a compound, composition or other material described by this phrase to significantly induce a positive modification in the condition being treated, but low enough to avoid significant side effects (e.g., significant skin irritation or sensitization), within the scope of sound judgment of the skilled artisan. The safe and effective amount of the compound, composition or other material may vary with the particular skin being treated, the age and physical condition of the biological subject being treated, the severity of the condition, the duration of the treatment, the nature of concurrent therapy, the specific compound, composition or other material employed, the particular cosmetically acceptable topical carrier utilized, and like factors within the knowledge and expertise of the skilled artisan.

As used herein, "cosmetically acceptable" means that a material (e.g., compound or composition) which the phrase describes is suitable for use in contact with the tissues of humans and lower animals without undue toxicity, incompatibility, instability, irritation, allergic response and the like.

As used herein, "regulating the oily and/or shiny appearance of skin" means preventing, retarding and/or arresting the appearance of oil and/or shine on the skin. By regulating the oily and/or shiny appearance of the skin, one or more of the following benefits are achieved: there is a noticeable decrease in the visible oil, shine, or highlights on the skin; the skin is substantially free from visible oiliness, shine, or highlights; the skin has a substantially matte finish; the user has a more uniform complexion. Regulating the oily and/or shiny appearance of the skin may result in more uniform and lasting coverage of the skin by the composition, increased wear resistance of the composition and/or a decrease in the incidence or severity of skin oil breaking through the composition so as to become visibly apparent.

Unless otherwise stated, all percentages herein are weight percentages based on the weight of the composition.

As used herein, "mixtures" is meant to include a simple combination of materials and any compounds that may result from their combination.

Primary Actives

The compositions of this invention comprise one or more suitable primary actives in an amount that is safe and effective for regulating the oily and/or shiny appearance of the skin. Suitable actives are those which effectively regulate the oily and/or shiny appearance of skin without unacceptably discoloring the skin, e.g., unacceptably causing reddening or flushing of the skin.

Compounds that possess significant vasodilatory properties are typically unsuitable for use as a primary active. Such vasodilatory compounds tend to cause unacceptable flushing or reddening of the skin such that their use, especially in facial applications, is not desirable. For example, known vasodilators such as nicotinic acid are not suitable for use herein.

Preferred compositions of this invention comprise as primary actives one or more compounds selected from the group consisting of niacinamide, pyridoxine, panthenol, pantothenic acid, and mixtures thereof. In a preferred embodiment, the primary actives are substantially pure. By substantially pure it is meant that the compound described by that phase is at least 90% pure, at least more preferably 95% pure, most preferably 99% pure.

In a preferred embodiment, the primary active comprises niacinamide, which is more preferably substantially pure niacinamide. Thus, the primary active may consist essentially of:

(a) niacinamide; or (b) a mixture of (i) niacinamide and (ii) one or more compounds selected from the group consisting of panthenol and pantothenic acid.

Preferably, the composition comprises from about 0.01% to about 20%, by weight, of primary active, more preferably from about 0.1% to about 10%, by weight, of primary active, even more preferably from about 1% to about 5%, by weight, of primary active, most preferably from about 2.5% to about 5%, by weight, of primary active, also from about 3% to about 5% primary active.

In an especially preferred embodiment, the topical composition comprises from about 2.5% to about 5%, by weight, of niacinamide, which is preferably substantially pure niacinamide.

Cosmetically Acceptable Carrier

The phrase "cosmetically acceptable carrier", as used herein, means one or more compatible solid or liquid fillers, diluents, extenders and the like, which are cosmetically acceptable as defined herein. The term "compatible", as used herein, means that the components of the compositions of this invention are capable of being comingled with the primary actives of the present invention, and with each other, in a manner such that there is no interaction which would substantially reduce the efficacy of the composition under ordinary use situations.

The type of carrier utilized in the present invention depends on the type of product desired. The topical compositions useful in the subject invention may be made into a wide variety of product types. These include, but are not limited to, lotions, creams, gels, sticks, sprays, ointments, pastes, mousses and cosmetics (e.g., solid, semi-solid, or liquid make-up, including foundations). These product types may comprise several types of carriers including, but not limited to, solutions, aerosols, emulsions (including oil-in-water or water-in-oil), gels, solids, and liposomes.

Solutions according to the subject invention typically include a cosmetically acceptable aqueous or organic solvent which is capable of having the primary active dispersed or dissolved therein. Water is a preferred solvent. Examples of suitable organic solvents include: propylene glycol, polyethylene glycol (e.g., Molecular Weight 200–600 g/mole), polypropylene glycol (e.g., Molecular Weight 425–2025 g/mole), glycerol, 1,2,4-butanetriol, sorbitol esters, 1,2,6-hexanetriol, ethanol, isopropanol, sorbitol esters, butanediol, and mixtures thereof. Solutions useful in the subject invention preferably contain from about 80% to about 99.99% of the aqueous or organic solvent and primary active in the above described amounts.

Aerosols according to the subject invention can be formed by adding a propellant to a solution such as described above. Exemplary propellants include chloro-fluorinated lower molecular weight hydrocarbons. Additional propellants that are useful herein are described in Sagarin, Cosmetics Science and Technology, 2nd Edition, Vol. 2, pp. 443–465 (1972), incorporated herein by reference. Aerosols are typically applied to the skin as a spray-on product.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317–324 (1986), each incorporated herein by reference.

The emulsion may also contain an anti-foaming agent to minimize foaming upon application to the skin. Anti-foaming agents include high molecular weight silicones and other materials well known in the art for such use.

Preferred emulsions have a low viscosity, of about 50 centistokes or less, more preferably about 10 centistokes or less, most preferably about 5 centistokes or less.

The topical compositions of the subject invention may comprise a topical cosmetically acceptable emollient. Such compositions preferably contain from about 2% to about 50% of the emollient. As used herein, "emollient" refers to a material used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of materials suitable as an emollient.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and primary active in the above described amounts. A cream typically comprises from about 5% to about 50%, preferably from about 10% to about 20%, of emollient; from about 45% to about 85%, preferably from about 50% to about 75%, water; and primary active in the above described amounts.

In addition to the primary active, ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and primary active in the above described amount.

Compositions of this invention useful for cleansing ("cleansers") are formulated with a suitable carrier, e.g., as described above, and preferably contain, in addition to the primary active in the above described amounts, from about 1% to about 90%, more preferably from about 5% to about 10%, of a cosmetically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in McCutcheon's Detergents and Emulsifiers, North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

As used herein, the term "foundations" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a cosmetically acceptable carrier for the primary active and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, incorporated herein by reference.

Such exemplary carriers and ingredients as described in application Ser. No. 08/430,961 include emulsions which contain a lipid or an oil. This oil (external) phase may comprise branched paraffins, hydrocarbons, esters, ethers, silicones and the like. Preferably the oil phase is comprised of volatile material and contains no "oils" as defined by the C.T.F.A. Cosmetic Ingredient Handbook, 3rd Ed., Cosmetic and Fragrance Assn., Inc., Washington D.C. (1982), incorporated herein by reference. More preferably, the oil phase comprises silicones, more preferably up to 90% of the oil phase is volatile silicones, non-volatile silicones and mixtures thereof. Still more preferably, these silicones are chosen from cyclomethicones and dimethicones and mixtures thereof. These materials are known in the art and are often commercially available. Thus, one of the most preferred oil phases can be considered, and is thus defined as a "silicone" phase and thus the foundation is defined as a "water-in-silicone" emulsion.

In such a "water-in-silicone" emulsion embodiment, a silicone is used in the oil phase and the silicone can comprise one or more volatile silicones, non-volatile silicones, and mixtures of volatile silicones and non-volatile silicones. The silicone is present in an amount of from about 1% to about 50% by weight of the composition. Suitable volatile silicones include cyclic and linear volatile polyorganosiloxanes (as used herein, "volatile" refers to those materials which have a measurable vapor pressure at ambient conditions). A description of various volatile silicones is found in Todd, et al. "Volatile Silicone Fluids for Cosmetics", 91 *Cosmnetics and Toiletries* 27–32 (1976). Preferred volatile silicones can include cyclic and linear polydimethylsiloxanes.

The volatile linear silicones generally have viscosities of less than about 5 centistokes at 25° C., while the volatile cyclic silicones typically have viscosities of less than about 10 centistokes. Some examples of volatile silicones useful in the present invention include: Dow Corning's 344, 345, 244, 245, and 200 silicones (manufactured by the Dow Corning Corporation): Silicone 7207 and Silicone 7158 (manufactured by the Union Carbide Corporation). SF1202 (manufactured by General Electric), Siloxane 5223 (available from Wacker Silicones) and the like. Of course, others are available and known in the art.

Furthermore, copending application Ser. No. 08/430,961 also describes useful emulsifiers for water-in-silicone emulsions which include polyoxylaklene copolymers. Such polymers are described in U. S. Pat. No. 4,268,499 as well which is incorporated herein by reference. Suitable copolymers are known and many are available commercially. A preferred emulsifier herein is known by its CTFA designation as dimethicones copolyol. Preferred emulsifiers are further disclosed by U.S. Pat. No. 5,143,722 which is incorporated herein by reference. The present compositions may comprise from about 0.5% to about 10%, preferably from about 1% to about 5%, more preferably from about 1.5% to about 3% of one or more emulsifiers.

With regard to suitable pigments described in copending application Ser. No. 08/430,961, there are no specific limitations as to the pigment, colorant or filler powders used in the composition. Each may be a body pigment, inorganic white pigment, inorganic colored pigment, pearling agent, and the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, nylon powder, polyethylene powder, methacrylate powder, polystyrene powder, silk powder, crystalline cellulose, starch, titanated mica, iron oxide titanated mica, bismuth oxychloride, and the like. These pigments and powders can be used independently or in combination.

It is preferred that the pigments are surface treated to provide added stability of color and ease of formulation. Hydrophobically treated pigments are more preferred, because they may be more easily dispersed in the oil phase. In addition, it may be useful to treat the pigments with a material that is compatible with a silicone phase. Particularly useful hydrophobic pigment treatments for use in water-in-silicone emulsions include polysiloxane treatments such as those disclosed in U.S. Pat. No. 5,143,722, incorporated herein by reference.

Filler powders can be used to modify the density, feel or thickness of the composition or as a matte finishing agent to hide skin defects and reduce shine. Such cosmetically acceptable agents include those disclosed in the C.T.F.A. Cosmetic Ingredient Handbook, 3rd Ed., Cosmetic and Fragrance Assn., Inc., Washington D.C. (1982), incorporated herein by reference. For example, spherical silica, hydrated silica, silicone-treated silica beads, mica, talc, polyethylene, bentonite, hectorite, kaolin, chalk, diatomaceous earth, attapulgite and the like may be utilized. Of the components useful as a matte finishing agents, low luster pigment, talc, polyethylene, hydrated silica, kaolin, titanium dioxide, titanated mica (mica coated with titanium dioxide) and mixtures thereof are preferred.

The compositions of the present invention may also be used specifically as film forming foundation compositions capable of providing superior feel, look and wear characteristics. Such compositions contain a film forming polymer/plasticizing solvent in the aqueous (internal) phase of the emulsion. This minimizes the unpleasant tacky sensation characteristic of polymers on the user's hands and fingers during the cosmetic's application. The combination of aqueous phase polymer and solvent is chosen to provide proper evaporation rate and polymer solvation for extension of the workability of the foundation and delay of any perceived onset of tackiness until after application is complete. Thus the judicious choice of plasticizing solvent, based upon the film forming polymer and evaporation rate, allows for the perceived tackiness to remain substantially imperceptible until the material has formed a film.

Typically, in such formulations, the pigment is presented in the oil phase to provide even coverage during initial application of the foundation. The aqueous phase of the emulsion is comprised of the film forming polymer, the plasticizing solvent, water soluble additives, and the like. Preferably, water can comprise up to about 60% by weight of the foundation composition. It is more preferred that water is present in the overall composition of the foundation in an amount of about 10% to about 50% by weight.

The film forming polymer which may used in the compositions of the present invention is compatible with the aqueous phase of the emulsion, and is incorporated in the internal phase of the water-in-oil emulsion, rather than in simple solution or in an oil-in-water emulsion. The polymer can be water dispersible, or water soluble, but is not a cross linked or a water swellable polymer. Of course, the polymer must be capable of forming a thin elastomeric film that physically adheres or interacts with the skin. The polymer film, when formed must also be water removable, that is easily removable with water and soap. It is preferred that the polymer be chosen so as not to be tacky.

The film forming polymer is formulated in the aqueous phase of the emulsion. The polymer is selected to provide a finished foundation preferably with a glass transition temperature (Tg) of about room temperature to about body temperature. "Glass transition temperature" or "Tg" refers to the temperature where the polymer softens or transitions from brittle to plastic, in the absence of plasticizers. This provides for a flexible polymer during application and wear. When the Tg is too high, the foundation may be hard to apply, and may flake. If it is too low, the foundation will be less adhesive (and perhaps more cohesive) and will tend to "ball up" on application.

Of course, the Tg of the polymer itself can vary. For example, it is expected that polymers with Tg of up to about 60° C. or higher are useful, provided the finished formulation has the proper Tg. For example polyvinylpyrrolidinone is thought to have a Tg greater than 90° C., but is useful in the invention. Typical polymers used in the invention are thermoplastic, rather than thermosetting.

Additionally, the polymer should be selected to provide an aqueous phase that is fluid enough to be handled and reasonably incorporated into the final emulsion composition as the dispersed or internal phase. Gelled and extremely viscous solutions can be used, but may impact ease of incorporation or final viscosity. Thus, it is preferred to select polymers which can be added at levels to derive film forming and extended benefits, while maintaining workability. of the final aqueous phase.

Examples of preferred polymers that have acceptable Tg, skin adhering properties and viscosity include, sulfopolyester resins, such as AQ sulfopolyester resins, such as AQ29D, AQ35S, AQ38D, AQ38S, AQ48S, and AQ55S (available from Eastman Chemicals), Vinex resins, such as Vinex 2034, Vinex 2144, and Vinex 2019 (available from Air Products), Dermacryl acrylic resins (available from National Starch), polyvinlypyrrolidinones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, and the like. Most preferred polymers include AQ38S and PVP. Typically the polymer is present in levels of from about 0.5% to about 10% by weight. More preferably, the polymer level is from about 1% to about 8% by weight.

Using the parameters defined above, and depending upon the choice of polymer, the preferred level of the polymer may vary. For example, when PVP is used as the film forming polymer, a still more prefered level is from about 1% to about 5% by weight. As another example, when the sulfopolyester AQ38S is used, the still more prefered level is from about 2% to about 8% by weight.

As used herein, the term "sulfopolyester resins," "sulfopolyester resin" or "AQ resin" refers to any of the AQ sulfopolyester resins, such as AQ29D, AQ35S, AQ38D, AQ38S, AQ48S and AQ55S, available from Eastman Chemicals, as described above.

As used herein, the term polyvinylacetate/polyvinyl alcohol polymer refers to such polymers as they are known in the art. Preferred examples of these are referred to as "Vinex" or "Vigex resins", available from Air Products, such as Vinex 2034, Vinex 2144, and Vinex 2019 described above.

As used herein the term water dispersible acrylic resins refers to those polymers as they are known in the art. "Dermacryl" is a preferred family of such acrylic polymer resins, available from National Starch, as Dermacryl LT and the like.

As used herein PVP refers to polyvinylpyrrolidones as they are known in the art. Their description, characterization and commercial designations is disclosed by E. S. Barabas in the *Encyclopedia of Polymer Science and Engineering*, 2 Ed. Vol. 17 pp. 198–257.

As used herein, "plasticizing solvent," includes slow evaporating, water miscible or dispersible cosolvents that are 1) generally recognized as safe (GRAS), many of these are listed in C.T.F.A. Cosmetic Ingredient Handbook, 3rd Ed., Cosmetic and Fragrance Assn., Inc., Washington D.C. (1982) pp. 575–580, incorporated herein by reference, or 2) include slow evaporating glycols and glycol ethers including for example, propylene glycol, butylene glycol, hexylene glycol, glycerine, dipropylene glycol, dipropylene glycol methyl ether (commonly known as DPM), propylene glycol phenyl ether, and polyethylene glycols (PEGs) such as PEG 4 and PEG 8, other classes of solvents include, propylene carbonate, and dimethyl isosorbide and mixtures thereof. More preferred solvents include propylene glycol, butylene glycol, propylene carbonate, dimethyl isosorbide and mixtures thereof. These solvents are generally present from about 0.5% to 30%, preferably from about 5% to 20% and generally appear in a ratio of solvent to polymer from about 10:1 to 1:1, more preferably from a ratio of about 8:1 to 2:1. Exact levels and ratios can be adjusted depending upon solvation, evaporation rate and the like.

The plasticizing solvent is chosen to provide for water co-solvency, suitable solubility regarding the polymer, low volatility, stability and of course safety (i.e., lack of toxicity). Thus the composition employs safe solvents that provide little or no sensation of tackiness, or cooling (usually due to evaporation) on the applied area. For example, any of the glycols are contemplated to be useful, including polyethylene glycols. These solvents also can be dipolar aprotic solvents that minimize hydrogen bonding and concomitant gelling and the like. For example, DMSO or DMF would be acceptable solvents, but for the safety concerns with the solvents.

Typically, the preferred polymer and plasticizing solvent are chosen such that the polymer and plasticizing solvent are in the aqueous phase of the emulsion. This diminishes any tacky sensation of polymer contacting the user's hands and fingers during the initial application of the composition. The solvent is chosen for its slow evaporation rate and its presence in the aqueous phase, and solvation properties. Typically it also extends the workability of the foundation and delays any perceived onset of tackiness for as long as possible, preferably up to two minutes.

The compositions of the present invention are preferably formulated to have a pH of 8 or below. The pH values of these compositions preferably range from about 2 to about 8, more preferably from about 3 to about 6, most preferably from about 4.5 to about 5.5.

Optional Ingredients

The compositions of this invention may contain other ingredients conventionally used in the art of skin care compositions, including but not limited to preservatives, preservative enhancers, and actives in addition to the primary actives. Any optional ingredients should be compatible with the primary active such that the activity of the primary active does not decrease unacceptably, preferably not to any significant extent, over a useful period (preferably at least about two years under normal storage conditions). For example, strong oxidizing agents may be incompatible with the primary active such that such agents are preferably avoided.

Other Actives

The compositions of the subject invention may optionally comprise other actives capable of functioning in different ways to enhance the benefits of the primary actives and/or to provide other benefits. Examples of such substances include, but are not limited to, anti-inflammatory agents, antimicrobial agents, anti-androgens, sunscreens, sunblocks, antioxidants/radical scavengers, chelators, depilation agents, desquamation agents, organic hydroxy acids, and natural extracts.

A. Anti-Inflammatory Agents

A safe and effective amount of an anti-inflammatory agent may be added to the compositions of the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, flucloronide acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, diclilorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammator Agents, Chemistry and Pharmacology*, 1, R. A. Scherrer, et al., Academic Press, New York (1974), each incorporated herein by reference.

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the cosmetically acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia particularly Rubia Cordifolia), and Guggal (extracted from plants in the genus Commiphora, particularly Commiphora Mukul), may be used.

B. Retinoids

A safe and effective amount of a retinoid may be added to the compositions of the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid. The retinoid is preferably retinol, retinal, or retinoic acid, more preferably retinoic acid.

The retinoids enhance the skin appearance benefits of the present invention. For example, the retinoids may diminish fine lines, wrinkles, or other textural discontinuities. Such benefits are themselves desirable and in the present invention, tend to also improve application of the present compositions.

C. Antimicrobial Agents

As used herein, "antimicrobial agent" means a compound capable of destroying microbes, preventing the development of microbes or preventing the pathogenic action of microbes. Antimicrobial agents are useful, for example, in controlling acne. A safe and effective amount of an antimicrobial agent may be added to compositions of the subject invention, preferably from about 0.001% to about 10%, more preferably from about 0.01% to about 5%, also from about 0.05% to about 2% or from about 0.05% to about 1% of the compositions. Preferred antimicrobial agents useful in the subject invention are benzoyl peroxide, erythromycin, tetracycline, clindamycin, azelaic acid, and sulfur resorcinol.

D. Antiandrogens

As used herein, "anti-androgen" means a compound capable of correcting androgen-related disorders by interfering with the action of androgens at their target organs. The target organ for the subject invention is mammalian skin.

E. Sunscreens and Sunblocks

Exposure to ultraviolet light can result in excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-methoxybenzophenone, octabenzone; 4-isopropyldibenzoylmethane; butylmethoxydibenzoyl-metlhane; etocrylene; [3-(4'-methylbenzylidene bornan-2-one) and 4-isopropyl-di-benzoylmethane.

Of these, 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl)) aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)4-aminobenzoic acid ester of 2-hydroxy-4-(2-hydroxyethoxy)benzophenone; and N,N-di-(2-ethylhexyl)-4-amninobenzoic acid ester of 4-(2-hydroxyethoxy)dibenzoylmethane and mixtures thereof.

Suitable inorganic sunscreens or sunblocks include metal oxides, e.g., zinc oxide and titanium dioxide. For example, the use of a titanium dioxide in topical sunscreen compositions that is applicable to the present invention is described in copending application Ser. No. 08/448,942, filed on May 24, 1995, in the names of Jiang Yue, Lisa R. Dew and Donald L. Bissett, incorporated herein by reference.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

F. Anti-Oxidants/Radical Scavengers

Preferred compositions of the subject invention include an anti-oxidant/radical scavenger as an active in addition to the primary active agents. The anti-oxidant/radical scavenger provides protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione) and dihydroxy fumaric acid and its salts may be used. Preferred anti-oxidants/radical scavengers are selected from tocopherol sorbate and other esters of tocopherol. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee, incorporated herein by reference.

G. Chelators

As used herein, "chelating agent" means an active agent capable of removing a metal ion from a system by forming a complex so that the metal ion cannot readily participate in or catalyze chemical reactions. The inclusion of a chelating agent provides protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the subject invention are furildioxime and derivatives thereof.

H. Organic Hydroxy Acids

The compositions of the present invention preferably comprise from about 0.1% to about 10%, more preferably from about 0.2% to about 5%, also preferably from about 0.5% to about 2%, of an organic hydroxy acid such as salicylic acid, glycolic acid, or lactic acid. Salicylic acid is preferred. The organic hydroxy acids enhance the skin appearance benefits of the present invention. For example, the organic hydroxy acids tend to improve the texture of the skin.

J. Desquamation Agents

A safe and effective amount of a desquamation agent may be added to the compositions of the subject invention, preferably from about 0.1% to about 10%, more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including but not limited to the organic hydroxy agents described above. One desquamation system that is suitable for use herein comprises certain sulfhydryl compounds and certain zwitterionic surfactants and is described in copending application Ser. No. 08/480,632, filed on Jun. 7, 1995 in the name of Donald L. Bissett, incorporated herein by reference. Another desquamation system that is suitable for use herein comprises salicylic acid and certain zwitterionic surfactants and is described in copending patent application Ser. No. 08/209,401, filed on Mar. 9, 1994 in the name of Bissett.

K. Depilation Agents

The compositions of the present invention may include a safe and effective amount of a depilation agent. When used, the composition preferably contains from about 0.1% to about 10%, more preferably from about 0.2% to about 5%, also preferably from about 0.5% to about 2% of depilation agent. A depilation agent preferred for use herein comprises certain sulfhydryl compounds, e.g., N-acetyl-L-cysteine. The use of such depilation agents is described in more detail in copending application Ser. No. 08/479,878, filed on Jun. 7, 1995, in the name of Greg G. Hillebrand and Vladimir Gartstein, incorporated herein by reference.

L. Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art. Skin lightening agents suitable for use herein also include those described in copending patent application Ser. No. 08/479,935, filed on Jun. 7, 1995 in the name of Hillebrand; and copending patent application Ser. No.08/390,152, filed on Feb. 24, 1995 in the names of Kalla L. Kvalnes, Mitchell A. DeLong, Barton J. Bradbury, Curtis B. Motley, and John D. Carter; both incorporated herein by reference.

M. Other Combination Actives

The compositions of the present invention may also include a natural extract of yeast, rice bran or the like such as are known in the art. Such extracts enhance the skin appearance benefits of the present invention, and are preferably used in an amount of from 0.1% to about 20%, more preferably 0.5% to about 10%, also from 1% to about 5%. A natural extract of yeast is preferred.

In a preferred embodiment, the compositions of this invention comprise niacinamide, panthenol or a mixture thereof as primary active and a natural extract, preferably a natural extract of yeast.

The compositions preferably comprise an oil absorbent such as are known in the art, e.g. clays (e.g. bentonite), microsponges, and Polytrap.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods For Regulating the Oily/Shiny Appearance of Skin

The subject invention relates to methods of regulating the oily and/or shiny appearance of skin. Such methods comprise topically applying to the skin to be treated an effective amount of the compositions of the subject invention so as to deposit an effective amount of primary active on the skin. The term "effective amount", as used herein, means an amount sufficient to regulate the oily and/or shiny appearance of skin as defined herein. In general, a safe and effective amount of the primary actives are left in contact with the skin for a period sufficient to provide noticeable effects, generally after chronic application such as described herein.

The composition can be applied for several days, weeks, months or years at appropriate intervals. The compositions are preferably applied from about four times a day to about once every three days, more preferably from about twice a day to once every other day, also about once a day, until a satisfactory oily and/or shiny skin appearance improvement has been achieved. The regulation of the appearance of oily and/or shiny skin can be observed visually without magnification. Methods of quantifying the regulation of the appearance of oily and/or shiny skin such as are known in the art can also be employed, e.g., sebutape analysis such as known in the art.

Typically, in each application, an effective coating of the skin with primary active is achieved by topically applying (in terms of mg active/cm² skin) from about 0.0002 mg/cm² to about 0.4 mg/cm² of primary active to the skin to be treated. More preferably, from about 0.002 mg/cm² to about 0.2 mg/cm² of primary active is applied. Most preferably, from about 0.02 mg/cm² to about 0.1 mg/cm² of primary active is applied (the amount of composition that is applied may be, for example, from about 0.01 mg to about 5 mg composition/cm² skin, preferably about 1 to about 2 mg composition/cm² skin).

The compositions are generally applied by lightly massaging the composition into the skin, typically in the amounts described above.

The compositions of the invention can also be used for regulating oiliness of the scalp and for controlling dandruff. Methods of regulating scalp oiliness and for controlling dandruff are as described above, wherein the composition is applied to the scalp.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

Example 1

A water-in-oil topical composition suitable for use as a liquid make-up foundation is prepared from the following ingredients using conventional mixing and formulating techniques such as described below.

| Compounding code | Ingredient | Wt. % |
|---|---|---|
| A | cyclomethicone | 9.25 |
| A | cetyl octanoate | 2.00 |
| A | dimethicone copolyol (DC3225C) | 20.00 |
| B | talc | 3.38 |
| B | pigment | 10.51 |
| B | Spheron L-1500 | 0.50 |
| C | Synthetic Wax Durachem 0602 | 0.10 |
| C | Arachidyl behenate | 0.30 |
| D | cyclomethicone | 1.00 |
| D | trihydroxystearin | 0.30 |
| E | laureth-7 | 0.50 |
| E | propyl paraben | 0.25 |
| F | fragrance | 0.05 |
| G | water | 34.44 |
| G | methyl paraben | 0.12 |
| G | propylene glycol | 8.00 |
| G | niacinamide | 4.00 |
| G | glycerin | 3.00 |
| G | sodium chloride | 2.00 |
| G | sodium dehydroacetate | 0.30 |

Combine the ingredients A and B in a suitable container. Mix the ingredients using a Silverson L4RT mixer equipped w/a 1" tubular assembly and a square hole screen for 30 minutes at 9000 rpm (the container can be covered to avoid loss of any volatile or other materials). Heat the resultant mixture to 85–90° C. Add ingredients C, mix for 5 minutes at 2100 rpm using a Silverson L4RT mixer equipped w/a 2" head and a disintegrating screen. The container should be covered to minimize evaporation of cyclomethicone and other volatile or nonvolatile materials. Cool the resultant mixture to 45–55° C.

Combine the ingredients D components and mix until a uniform slurry is formed. Separately, combine the ingredients E and mix until a uniform slurry is formed. Add the resultant slurries to the mixture of A, B and C (which is at 45–55° C.), mix for 5 minutes at 2100 rpm using a Silverson L4RT equipped w/a 2" head and a disintegrating screen. Cool the resultant mixture to 30° C., then add ingredient F. Mix 5 minutes at 2100 rpm using a Silverson L4RT equipped w/a 2" head and a disintegrating screen.

Combine the ingredients G in a suitable container and mix until all components are dissolved. Slowly add the resultant solution to the mixture of A-F. Emulsify this combination using a Silverson L4RT mixer equipped w/a 2" head and a disintegrating screen at 2100–5100 rpm (rpms will increase as the mixture thickens), continue mixing for 5 minutes after all of the G mixture is added.

Apply the composition to a person's face once per day in an amount of 1–2 mg composition/cm² skin for four weeks, to observe a decrease in facial oil, a reduction in oily breakthrough, longer wear of the foundation, and more even coverage as the time period passes.

Other topical compositions suitable for use as a foundation are prepared in the above-described manner using pyridoxine, panthenol or pantothenic acid in place of niacinamide and are applied to the face as described above.

Example 2

A topical composition suitable for use as a liquid make-up foundation is prepared from the following ingredients using conventional mixing and formulating techniques.

| | wt % |
|---|---|
| dimethicone copolyol/cyclomethicone (Dow Corning QZ-3225C) | 10 |
| cyclomethicone (Dow Corning 344 fluid) | 17.74 |
| pigments | 3.7 |
| titanium dioxide | 8.25 |
| trihydroxy stearin | 0.3 |
| aqueous floral extract | 0.01 |
| denatured ethanol | 4–17 |
| salicylic acid | 1.45 |
| dipropylene glycol | 0–14 |
| PVP (polymeric dispersing agent) | 1 |
| procetyl AWS (PPG-5 ceteteth, surfactant) | 3 |
| tri-sodium citrate | 0.3 |
| tetrasodium EDTA | 0.1 |
| glycerin | 10–30 |
| niacinamide | 4 |
| sodium chloride | 0.3 |
| water | 15.85–34.85 |

Apply the composition to a person's face once per day in an amount of 1–2 mg composition/cm² skin for four weeks, to observe a decrease in facial oil and/or shine, a reduction in oily breakthrough, longer wear of the composition, and more even coverage as time passes.

Other topical compositions suitable for use as a foundation are prepared in the above-described manner using pyridoxine, panthenol or pantothenic acid in place of niacinamide and are applied to the face as described above.

Example 3

Moisturizers having the compositions A, B or C are prepared from the following ingredients using conventional mixing and formulating techniques.

| Ingredient | A wt % | B wt % | C wt % |
|---|---|---|---|
| Water | 68.3 | 70.3 | 75.3 |
| niacinamide | 5 | 5 | 0 |
| Panthenol | 1.5 | 1.5 | 1.5 |
| acrylates copolymer (DC Polymer powder Q5-6603) | 2 | 0 | 0 |
| Octyl Methoxycinnamate (Parsol MCX) | 4 | 4 | 4 |
| Glycerin | 5 | 5 | 5 |
| Propylene Glycol | 1.1 | 1.1 | 1.1 |
| Isohexadecane (Permethyl 101 A) | 2 | 2 | 2.00 |
| Tocopheryl Acetate | 2 | 2 | 2.00 |
| herbal extract in propylene glycol & ethoxydiglycol | 1 | 1 | 1 |
| Butylene Glycol | 1 | 1 | 1 |
| Dimethicone (DC 200 Fluid 1000 cs) | 1 | 1 | 1 |
| Cyclomethicone (DC 344 Silicone Fluid) | 1 | 1 | 1 |
| Triethanolamine | 0.8 | 0.8 | 0.8 |
| Cetyl Palmitate (Cutina CP) | 0.75 | 0.75 | 0.75 |
| Tribehenin (Syncrowax HRC) | 0.75 | 0.75 | 0.75 |
| Stearoxytrimethylsilane & Stearyl Alcohol (DC 580 Wax) | 0.5 | 0.5 | 0.5 |
| Phenoxyethanol | 0.62 | 0.62 | 0.62 |
| Carbomer (Carbopol 954) | 0.3 | 0.3 | 0.3 |
| Hectorite (Bentone EW) | 0.3 | 0.3 | 0.3 |
| Acrylates/C10–C30 Alkyl Acrylate Crosspolymer (Pemulen TR 1) | 0.2 | 0.2 | 0.2 |
| Potassium Cetyl Phosphate (Amphisol K) | 0.2 | 0.2 | 0.2 |
| Perfume | 0.2 | 0.2 | 0.2 |
| Disodium EDTA | 0.1 | 0.1 | 0.1 |
| Xanthan Gum | 0.07 | 0.07 | 0.07 |
| preservative | 0.25 | 0.25 | 0.25 |

Apply the composition to a person's face once per day in an amount of 1–2 mg composition/cm$^2$ skin for four weeks, to observe a decrease in facial oil and/or shine.

Other compositions are prepared in the above-described manner using pyridoxine, panthenol or pantothenic acid in place of niacinamide and are applied to the face as described above.

Example 4

A silicone gel containing 2 or 4% niacinamide is prepared from the following ingredients using conventional mixing and formulating techniques.

| | wt % |
|---|---|
| water | 89.6–91.6 |
| niacinamide | 2 or 4 |
| glycerin | 2.08 |
| cyclomethicone (Dow Corning 344 fluid) | 1.22 |
| butylene glycol | 1 |
| cyclomethicone and dimethiconol (Dow Corning Q2-1401) | 0.58 |
| cyclomethicone and dimethicone copolyol (Dow Corning QZ-3225C) | 0.58 |
| dimethicone copolyol (Dow Corning 193 polyether) | 0.12 |
| acrylates/C10–30 alkylacrylates crosspolymer (Pemulen TR-1) | 0.25 |
| carbomer (Carbopol 980) | 0.2 |
| DMDM hydantoin and iodopropynyl butyl carbamate (Glydant Plus) | 0.2 |
| disodium EDTA | 0.1 |
| sodium hydroxide | 0.08–0.1 to total 100 |

Apply the gel to a person's face once per day in an amount of 1–2 m gel/cm$^2$ skin for four weeks, to observe a decrease in facial oil and/or shine.

Other silicone gels are prepared in the above-described manner using pyridoxine, panthenol or pantothenic acid in place of niacinamide and are applied to the face as described above.

Example 5

A liquid shampoo having the composition A, B or C is prepared by combining the following components using conventional mixing and formulating techniques:

| | A (wt %) | B (wt %) | C (wt %) |
|---|---|---|---|
| coconut oil | 14 | 18 | — |
| olive oil | 3 | — | — |
| castor oil | 3 | 4 | — |
| potassium hydroxide, 85% | 4.7 | 5.3 | — |
| glycerol | 2 | 4 | 5 |
| ethyl alcohol | 4 | — | 10 |
| sodium hexametaphosphate | 1 | — | — |
| perfume | 0.3 | 0.2 | q.s. |
| water | 64 | 64 | 36 |
| borax | — | 0.5 | — |
| coconut soap potassium salt | — | — | 35 |
| olive oil soft soap | — | — | 10 |
| niacinamide | 4 | 4 | 4 |

Apply the shampoo to the scalp every other day to once a day to reduce the appearance of oily hair and the occurrence of dandruff. A dose of about 0.5 ml is applied and washed off.

Other liquid shampoos are prepared in the above-described manner using pyridoxine, panthenol or pantothenic acid in place of niacinamide and are applied to the scalp as described above.

Example 6

A hair conditioner is prepared by combining the following components using conventional mixing and formulating techniques:

| | wt % |
|---|---|
| PVP K-30 (polymeric dispersing agent) | 3 |
| Neobee M-20 (propylene glycol dicaprylate) | 5 |
| Drewmulse 1128 (surfactant) | 5 |
| water | 69.5 |
| triethanolamine | 1 |
| carbopol 934 (carbomer, polymeric thickening/dispersing agent) | 1 |
| WSP-X250 | 5 |
| Amerchol L-101 (mineral oil/lanolin oil) | 3 |
| Lipal 15 CSA | 3 |
| preservative | q.s. |
| perfume | 0.5 |
| niacinamide | 4 |

Apply the conditioner to the scalp, preferably to clean hair, every other day to once a day to reduce the appearance of oily hair and the occurrence of dandruff. Apply a dose of about 0.5 ml and wash off.

Other hair conditioners are prepared in the above-described manner using pyridoxine, panthenol or pantothenic acid in place of niacinamide and are applied as described above.

Example 7

A bath oil having the composition A, B or C is prepared by combining the following components using conventional mixing and formulating techniques:

|                        | A (wt %) | B (wt %) | C (wt %) |
|------------------------|----------|----------|----------|
| POE 20 sorbitan monopalmitate | —    | 5        | 22.2     |
| fragrance oil          | 35       | 5        | 4.4      |
| isopropyl myristate    | 65       | —        | —        |
| methyl p-hydroxybenzoate | —      | 0.18     | —        |
| propyl p-hydroxybenzoate | —      | 0.02     | —        |
| sodium lauryl sulfate  | —        | —        | 10       |
| ninol AA-63            | —        | —        | 1        |
| sorbic acid            | —        | —        | 0.2      |
| niacinamide            | 4        | 4        | 4        |
| water q.s.             | —        | 100      | 100      |

Apply the bath oil to the skin either as prepared or in aqueous diluted form. Apply in a dose of from 1–2 mg oil/cm$^2$ skin for four weeks, to observe a decrease in skin oil and/or shine. Other bath oils are prepared in the above-described manner using pyridoxine, panthenol or pantothenic acid in place of niacinamide and are applied as described above.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A topical composition for regulating the oily and/or shiny appearance of mammalian skin, the composition comprising a water-in-oil emulsion, said emulsion comprising:

(a) an oil phase comprising from about 1% to about 50%, by weight, of a silicone selected from the group consisting of cyclomethicone, dimethicone and mixtures thereof;

(b) from about 1% to about 10%, by weight, an active for regulating the oily and/or shiny appearance of mammalian skin, said active consisting essentially of niacinamide, pantothenic acid, and mixtures thereof;

(c) from about 3% to about 30%, by weight, of glycerin;

(d) from about 0.5% to about 10%, by weight, of dimethicone copolyol;

(e) a pigment;

(f) a spherical silica;

(g) from about 0.5% to about 10% of a film-forming polyhmer selected from the group consisting of sulfopolyester resins, Vinex resins, Dermacryl acrylic resins, polyvinylpyrrolidones, polyvinylpyrrolidone/vinyl acetate copolymer, polyvinylpyrrolidone/dimethylaminoethylmethacrylate copolymer; and (h) an aqueous phase comprising water.

2. The composition of claim 1 comprising from about 1% to about 5%, by weight, of the active.

3. The composition of claim 1 comprising from about 2.5% to about 5%, by weight, of the active.

4. The composition of claim 1 wherein the active for regulating the oily and/or shiny appearance of mammalian skin consists essentially of niacinamide.

5. The composition of claim 1 wherein said composition further comprises an active selected from the group consisting of sunscreens, sunblocks, anti-oxidants, radical scavengers, retinoids, and mixtures thereof.

* * * * *